Figure 1:
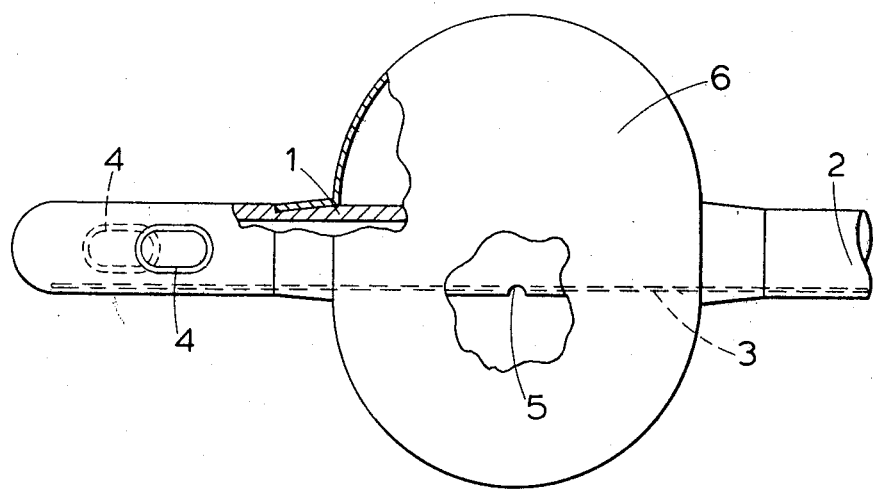

United States Patent [19]
Briggs et al.

[11] 4,263,236
[45] Apr. 21, 1981

[54] METHOD FOR PRODUCING CATHETERS

[75] Inventors: Peter J. Briggs, Lancing; Steven Carpenter, Chichester, both of England

[73] Assignee: Matburn (Holdings) Limited, London, England

[21] Appl. No.: 935,163

[22] Filed: Aug. 21, 1978

[30] Foreign Application Priority Data

Aug. 25, 1977 [GB] United Kingdom ............... 35679/77

[51] Int. Cl.³ .............................................. B32B 1/10
[52] U.S. Cl. .................... 264/26; 156/294; 156/298; 264/25; 264/248; 264/249
[58] Field of Search .................. 264/25, 26, 248, 249, 264/129, 134, 135; 156/294, 298; 128/349 B

[56] References Cited

U.S. PATENT DOCUMENTS

| 1,810,896 | 6/1931 | Grubman ......................... 264/249 X |
| 3,128,504 | 4/1964 | Gewecke ......................... 264/248 X |
| 3,528,869 | 9/1970 | Dereniuk ......................... 264/250 X |
| 3,734,100 | 5/1973 | Walker et al. ............... 128/349 B X |
| 3,884,242 | 5/1975 | Bazell et al. ................ 128/349 B X |

Primary Examiner—Jan H. Silbaugh
Attorney, Agent, or Firm—McAulay, Fields, Fisher, Goldstein & Nissen

[57] ABSTRACT

A catheter with an inflation cuff, is produced by a method in which an inflation cuff of an elastomeric material which is not thermoplastic is placed on a catheter shaft of thermoplastic material at a desired position. Pressure is directed inwardly around the entire periphery of at least each end of the cuff. The shaft is heated sufficiently to soften it so as to enable at least the ends of the cuff to be recessed into the material of the shaft by the inwardly directed pressure.

7 Claims, 2 Drawing Figures

METHOD FOR PRODUCING CATHETERS

BACKGROUND OF THE INVENTION

Surgical catheters of the kind having an inflation cuff or balloon near one end are known. One such catheter is called a Foley catheter. Although the invention is particularly applicable to the production of Foley catheters it can be applied to other types of inflation catheters for example aortic catheters, irrigation catheters, endotracheal tubes or to simple occlusion tubes. Such tubes are herein considered to be embraced by the term "catheter".

Such catheters have inflation cuffs on the catheter shafts. This leads to a problem in that the completed article has a ridge or "step" at each end of the cuff. Many ways have been proposed for avoiding such steps, but none of the known ways have proved to be entirely satisfactory.

An object of the invention is to provide a way of producing a catheter in which at least the ends of the inflation cuff are recessed into the catheter shaft.

BRIEF SUMMARY OF THE INVENTION

The invention provides a method for producing a catheter with an inflation cuff comprising the steps of placing an inflation cuff of an elastomeric material which is not thermoplastic on a catheter shaft of a thermoplastic material at a desired position, applying inwardly directed pressure around the entire periphery of at least each end of the cuff, and heating the shaft sufficiently to soften it so as to enable at least the ends of the cuff to be recessed into the material of the shaft by the said inwardly directed pressure. The pressure is preferably provided by means of a collar or collars arranged to surround the ends of the cuff after it has been fitted on the shaft. The recess formed in the shaft may be of such depth that the ends of the cuff are completely recessed in, i.e. are flush with the surface of, the shaft or the ends may be only partly recessed in the shaft. Obviously the material to the shaft must be such that it will soften at a temperature which is below the temperature required to destroy or impair the desired properties of the inflation cuff. It is preferred that the shaft be made of polyvinylchloride (PVC) and the material of the cuff is of natural rubber.

Although it is preferred to make the shaft of PVC, other thermoplastic materials may be used such as, for example polyvinyldichloride, ethylene vinylacetate, polypropylene, polyethylene. Although it is preferred to make the inflation cuff of natural rubber it can, alternatively, be made of any suitable elastomeric material which is not thermoplastic such as polychloroprene, polyisoprene, butadiene-acrylonitrile or styrene-butadiene co-polymers, silicone polymers or non-thermoplastic polyurethane. Composites or laminates of any of these materials may also be used.

BRIEF DESCRIPTION OF THE ACCOMPANYING DRAWINGS

Figure 2:
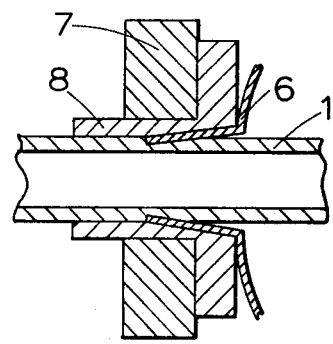

FIG. 1 is a sectional view of part of a catheter made by the method of the invention, and FIG. 2 is a schematic sectional view of a heating means used in the method of the invention.

DESCRIPTION OF ONE EMBODIMENT OF THE INVENTION

A Foley catheter has a catheter shaft 1 made of PVC. The shaft has a drainage lumen 2 and an inflation lumen 3, these lumens running substantially all the length of the shaft. The drainage lumen 3 opens near one end of the shaft, called the distal end, in two drainage eyes 4. The inflation lumen opens in an outlet or eye 5 near the distal end. At the other end of the shaft (not illustrated), called the "proximal end", is fixed a member containing two tubes one of which leads into the drainage lumen and the other of which leads into the inflation lumen. These two tubes are conveniently arranged as a Y-piece.

An inflation cuff 6 of latex rubber is fitted over the outside of the shaft 1 in such a position that the eye or opening 5 leading from the inflation lumen 3 near the distal end of the catheter is covered by the cuff 6. When the cuff 6 is in position each end of the cuff is surrounded by a collar 7 one of which is shown in FIG. 2. Each collar 7 fits tightly around the cuff 6 thereby to squeeze or apply inwardly directed pressure on the cuff 6 and shaft 1. Any suitable means are provided to prevent any occlusion or reduction in the cross-sections of the lumen; conveniently, mandrels (not shown) can be inserted in the drainage lumen 2 and in the inflation lumen 3. The areas of the cuff surrounded by the collar 2 are connected to an appropriate source of heat. The heating may, for example, be effected by induction or, where suitable, by a radio frequency system, or the collar may be heatable collars which directly apply heat to the cuff and shaft. The shaft 1 will soften under the heat applied and due to the inward pressure exerted by the collar 7 on the cuff and the shaft, the ends of the cuff will produce a recess in the softened material of the shaft. Such recess may be of sufficient depth for the surface of the cuff at each end to be flush with the surface of the remainder of the shaft as shown in FIG. 1 or the ends of the cuff may be only partially recessed in the shaft. If desired, a single collar can surround the entire cuff in which case the application of heat and pressure will cause the cuff to be recessed over the entire length in the surface of the shaft.

The collar 7 has an internal lining 8 which tapers towards one end. A lining 8 is not always essential, but if there is no lining the collar must be internally tapered.

The heating step can be applied before or after the cuff 6 is secured to the shaft 1 by an adhesive. Preferably, the adhesive is applied before the heating step. Alternatively, however, the recessing can be produced before the adhesive is applied in which case the ends of the cuff are turned back, the adhesive is applied and the ends are then folded back into position. In another possibility, an adhesive is applied to the shaft and/or to the appropriate part of the cuff, and is allowed to dry. The cuff is then assembled on the shaft and the adhesive will be reactivated to form a bond during the operation to recess the cuff into the shaft.

What is claimed is:

1. A method for producing a catheter with an inflation cuff, said method comprising the steps of:
   (a) placing an inflation cuff of an elastomeric material which is not thermoplastic at a desired portion on a catheter shaft of thermoplastic material,
   (b) applying a preselected material to the interior of said shaft to prevent the collapse thereof,
   (c) heating the shaft sufficiently to soften it, and (d) moving the ends of said cuff into said softened shaft by applying inwardly directed pressure around the entire periphery of at least each end of said cuff to force the ends of said cuff into the material of said shaft to form recesses by displacing the shaft material with the cuff ends thereby to form a smooth transition at the junction of said cuff ends and said shaft.

2. A method as claimed in claim 1, wherein the pressure is applied by surrounding the ends of the inflation cuff, after it has been positioned on the catheter shaft, by at least one collar fitted tightly around the cuff thereby to squeeze and direct pressure inwardly on the cuff and the shaft.

3. A method as claimed in claim 2, wherein the catheter shaft is polyvinylchloride, polyvinyldichloride or ethylene vinylacetate and the inflation cuff is of natural rubber.

4. A method as claimed in claim 3, wherein the shaft is heated by radio frequency heating.

5. A method as claimed in claim 4, wherein the collar has an internal lining which tapers towards one end.

6. A method as claimed in claim 1, wherein the pressure and heat applied to the cuff and shaft is arranged to produce recesses in the shaft at each end of the cuff, the recesses tapering towards the ends of the cuff and each having a depth at the end of the cuff such that the end portion of the cuff is flush with the surface of the shaft.

7. A method as claimed in claim 6, wherein the ends of the cuff are secured to the shaft by an adhesive prior to the application of heat and pressure.

* * * * *